United States Patent [19]

Fuhrman et al.

[11] Patent Number: 5,470,885
[45] Date of Patent: Nov. 28, 1995

[54] FLUOROCARBONS AS ANTI-INFLAMMATORY AGENTS

[75] Inventors: Bradley P. Fuhrman, Buffalo, N.Y.;
Stephen F. Flaim, San Diego, Calif.;
Lynn J. Hernan, Buffalo, N.Y.;
Frances D. Nesti, Shelburne, Vt.;
Michele C. Papo, Buffalo; David M.
Steinhorn, Eggertsville, both of N.Y.

[73] Assignee: The Research Foundation of the State University of New York, Albany, N.Y.

[21] Appl. No.: 128,811

[22] Filed: Sep. 29, 1993

[51] Int. Cl.$^6$ .............................. A61K 9/12; A61L 9/04; A61M 15/00; A61M 15/08
[52] U.S. Cl. .......................... 514/743; 514/759; 514/848; 514/886; 514/887; 514/959; 128/204.18
[58] Field of Search ...................... 128/204.18; 514/959, 514/848, 886, 887, 743, 759

[56] References Cited

U.S. PATENT DOCUMENTS

| | | | |
|---|---|---|---|
| 4,044,121 | 8/1977 | Ko | 424/47 |
| 4,543,202 | 9/1985 | Bartlett et al. | 424/609 |
| 4,680,173 | 7/1987 | Burger | 424/47 |
| 4,865,836 | 9/1989 | Long, Jr. | 514/832 |
| 4,897,262 | 1/1990 | Nandagiri et al. | 424/78 |
| 4,927,623 | 5/1990 | Long, Jr. | 514/772 |
| 4,987,154 | 1/1991 | Long, Jr. | 514/832 |
| 5,028,428 | 7/1991 | Smith et al. | 514/886 |
| 5,192,528 | 3/1993 | Radhakrishnan et al. | 424/450 |
| 5,213,570 | 5/1993 | VanDeripe | 604/28 |
| 5,225,183 | 7/1993 | Purewal et al. | 424/45 |
| 5,284,645 | 2/1994 | Long | 424/450 |
| 5,290,540 | 3/1994 | Prince et al. | 514/959 |

FOREIGN PATENT DOCUMENTS

WO92/19300  11/1992  WIPO.

OTHER PUBLICATIONS

Calderwood, et al., "Residual Levels and Biochemical Changes after Ventilation with Perfluorinated Liquid", *J. Appl. Physiol.*, 34:4, pp. 603–607, 1975.
Forman, et al., "A Fine Structure Study of the Liquid–Ventilated Newborn Rabbit Lung", *Federation Proc.* 43:647, Abstract 2118.
Modell, et al., "Liquid Ventilation of Primates", *Chest* 69: pp. 79–81, 1976.
Modell, et al., "Long–Term Survival of Dogs after Breathing Oxygenated Fluorocarbon Liquid", *Federation Proceedings* 29:5 pp. 1731–1739, 1970.
Jean G. Riess, "Reassessment of Criteria for the Selection of Perfluorochemicals for Second–Generation Blood Substitutes: Analysis of Structure/Property Relationships", *Artificial Organs* 8:1 pp. 44–56, 1984.
Hirschl, et al., The FASEB Journal 7(3): p. A229, 1993.

*Primary Examiner*—Ronald W. Griffin
*Attorney, Agent, or Firm*—Knobbe, Martens, Olsen & Bear

[57] ABSTRACT

A method for reducing the inflammatory response in tissue of a patient, by contacting the tissue with an effective, inflammation-reducing amount of a liquid or gaseous fluorocarbon.

10 Claims, 3 Drawing Sheets

FLUOROCARBONS AS ANTI-INFLAMMATORY AGENTS

FIELD OF THE INVENTION

This invention relates to the use of gaseous or liquid fluorocarbons in preventing or treating inflammation in various tissues.

BACKGROUND OF THE INVENTION

The reticuloendothelial system (RES) is a network of phagocytic cells called macrophages which are derived from circulating leukocytes called monocytes. These circulating monocytes differentiate into tissue macrophages which become localized to organs including the spleen, liver and lungs. Tissue macrophages engulf foreign bodies and promote their clearance by other components of the humoral immune system. Alveolar macrophages provide a first line of cellular defense against invasion of the lung by inhaled foreign material and pathogens. After tissue injury, compounds are released that promote migration of neutrophils and macrophages to the wound site. These cells then release inflammatory mediators and cytokines including interleukins, complement components, prostaglandins, interferons, peroxides and free radicals which begin an inflammatory cascade. Although this cascade is mostly beneficial as in destroying bacterial pathogens, in some cases it is inappropriately excessive and leads to severe disorders.

Adult respiratory distress syndrome (ARDS) is a serious condition most often affecting the lungs of individuals who have undergone major surgery, trauma or infection. ARDS occurs in approximately 150,000 persons annually with a mortality rate approaching 50%. Lung injury results in leukocyte influx. These leukocytes then release inflammatory cytokines resulting in accumulation of fluid and cellular debris in the pulmonary passages, thus impairing oxygen exchange. There is currently no completely effective treatment for this disorder. Infant Respiratory Distress Syndrome (IRDS) presents similar treatment difficulties. Symptomatic treatment through liquid breathing of fluorocarbons has been proposed as a means to facilitate oxygen delivery and remove accumulations in the lung in ARDS and IRDS. See, e.g., PCT application PCT/US92/03660.

Fluorocarbon (FC) liquids are generally analogous to common organic compounds; however, most or all of the carbon-bound hydrogen atoms have been replaced with fluorine atoms. These compounds are typically clear, colorless, odorless, nonflammable and essentially insoluble in water. When all carbon-bound hydrogens have been replaced with fluorine, the compounds are referred to as perfluorocarbons (PFCs). PFC liquids are denser than water and soft tissue, have low surface tension and low viscosity. PFC liquids and other highly fluorinated liquids are unique in their high affinity for gases, dissolving more than 20 times as much oxygen and over three times as much carbon dioxide as water. PFC liquids are also substantially nontoxic and inert (Riess, (1984) *Artificial Organs*, 8: 34–56). One example of a widely-used perfluorocarbon is perfluorooctyl bromide (PFOB), also called perflubron. These liquids are commonly used as either neat solutions or emulsions.

Mammals can breathe oxygenated FCs and return to air breathing without long-term effects (Modell et al., (1970) *Federation Proc.*, 29: 1731–1739; Modell et al., (1976) *Chest*, 69: 79–81). No significant adverse morphological, biochemical or histological effects are observed after FC ventilation (Calderwood et al., (1975) *J. Applied. Physiol.*, 39: 603–607; Forman et al., (1984) *Federation Proc.*, 43: 647). Published PCT application PCT/US91/07142 to Fuhrman describes a perfluorocarbon associated gas exchange (PAGE) method which maintains respiratory gas exchange in the PFC-laden pulmonary air passages by continuous positive pressure breathing using a conventional gas ventilator. This procedure allows more rapid ventilation and is far less cumbersome than liquid breathing. PFCs are effective in rinsing out cellular debris associated with ARDS (Puchetti et al., (1984) *Fourth World Congress for Bronchology*, abstract, 115) and in treating respiratory distress syndromes involving surfactant deficiency or dysfunction. A number of other biomedical applications for liquid PFCs and PFC emulsions have also been described, including their use as imaging agents and blood substitutes (Riess, (1984) *Artificial Organs*, 8: 34–56). Liquid PFCs are removed from the circulation by macrophages of the RES.

SUMMARY OF THE INVENTION

Figure 1:
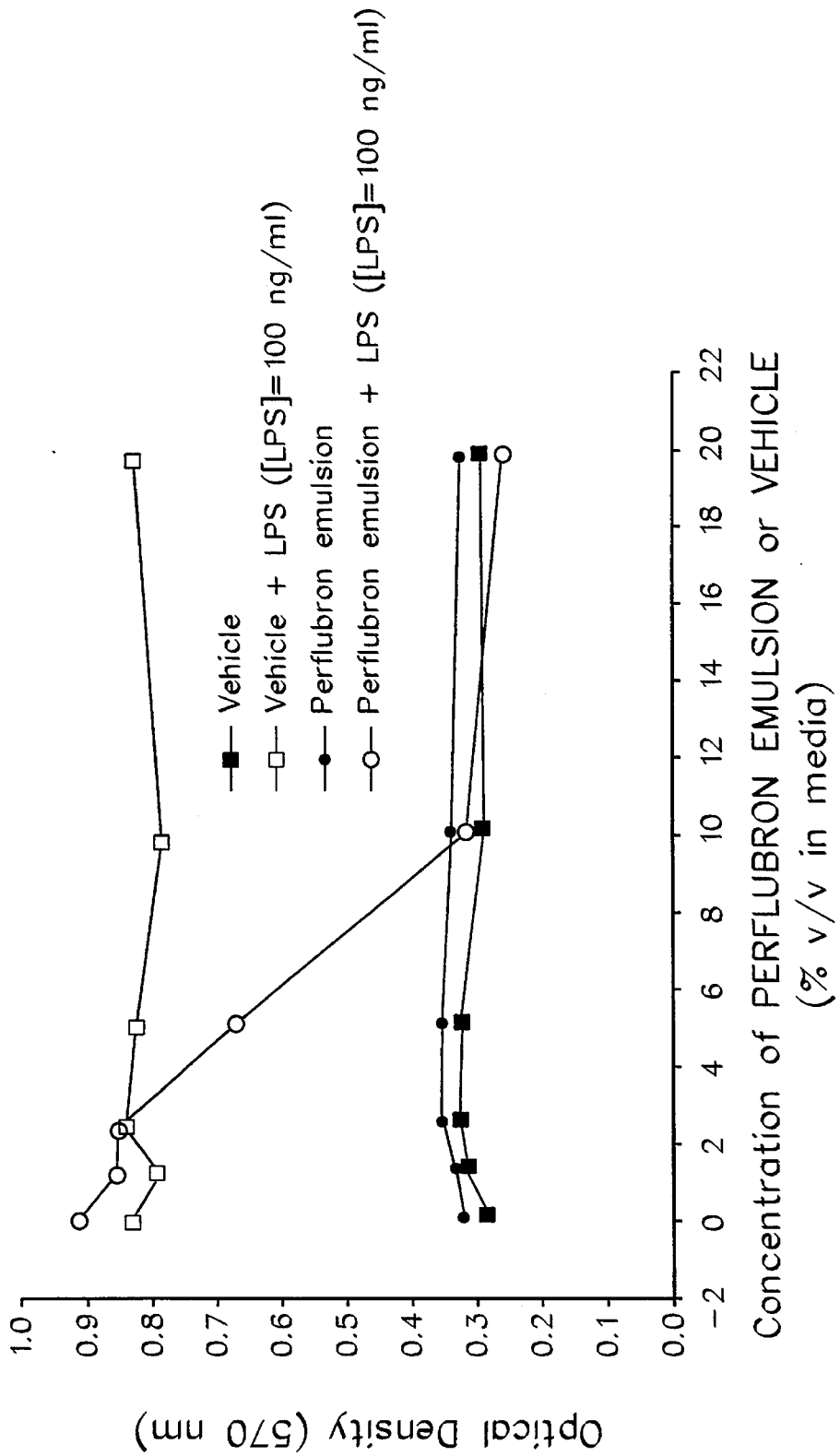
FIG. 1 shows the effect of perfluorooctyl bromide (PFOB) emulsion on LPS-induced ICAM-1 expression. The x-axis indicates the concentration of PFOB (perflubron) emulsion or vehicle (emulsifying agents with no PFOB; % v/v in media) and the y-axis indicates the optical density at 570 nm.

The present invention provides a method for reducing the inflammatory response in the tissue of a patient in need of such treatment by contacting the tissue with an effective, inflammation-reducing amount of a liquid or gaseous fluorocarbon. Both prophylactic reductions and therapeutic reductions of inflammatory response are contemplated. Preferably, this tissue is either gastrointestinal or pulmonary, the cellular nature of which may be either epithelial or endothelial. According to another aspect of the invention, the inflammation is associated with either adult respiratory distress syndrome or infant respiratory distress syndrome. The fluorocarbons of the present invention may further comprise a mixture of different liquid or gaseous fluorocarbons. In another embodiment, the fluorocarbon is administered in the form of a gas which may also be mixed with a breathing gas. In still another embodiment, the fluorocarbon is administered in the form of droplets suspended in a gas. According to another aspect of the present invention the fluorocarbon is administered into the lungs in the form of a liquid and the patient breathes an oxygenated gas following the administration and while the patient is breathing liquid fluorocarbon. The invention also provides oxygenation of the liquid fluorocarbon prior to administration and further provides fluorocarbons in the form of emulsions.

The present invention also provides an apparatus for use in delivering fluorocarbon to the lungs of a patient, comprising a container, a fluorocarbon liquid in the container, and means associated with the container for atomizing, aerosolizing, or vaporizing a unit dosage of the fluorocarbon for inhalation by a patient.
}

DETAILED DESCRIPTION OF THE INVENTION

The present invention provides a method of prevention (prophylactic) or treatment (therapeutic) of the acute inflammation associated with pulmonary and other mucosal, local, or systemic inflammatory disorders by administration of fluorocarbons to the site of the inflammation. For example, perfluorooctyl bromide (PFOB) inhibited bacterial endotoxin (LPS)-induced activation of HUVEC cells (Example 1), depressed macrophage phagocytic activity in vitro (Example 2) and significantly improved the inflammatory condition associated with gastric acid aspiration-induced ARDS in vivo (Example 3). The depression of macrophage activity inhibited free radical and $H_2O_2$ production by alveolar macrophages in vitro (Example 4) and will also inhibit the release of inflammatory mediators, thus improving the course of pulmonary and systemic inflammatory disorders. It appears that the activation of macrophages and circulating blood leukocytes is directly affected by fluorocarbons, thus these cell types can be treated directly to reduce their inflammation-promoting activities.

Although Example 3 describes the use of PFOB in the treatment of ARDS, the use of fluorocarbons in the treatment of a number of pulmonary and systemic inflammatory conditions is within the scope of the present invention. These disorders include, for example, infant respiratory distress syndrome, asthma, cystic fibrosis, systemic lupus erythematosus, rheumatoid arthritis, Crohn's disease, colitis, sepsis, peritonitis, vasculitis, allergic reactions, collagen vascular disease, diverticulitis, endometriosis and other autoimmune disorders. A particularly preferred application of the present invention is the treatment of mucosal inflammation, including the pulmonary, gastrointestinal, and vaginal mucosa.

In the prior art, fluorocarbon liquids have been proposed for treatment of respiratory distress syndrome by removal of lung debris, inflammatory cells and materials by lavage, and by facilitating oxygen delivery. In contrast, the present invention is directed toward prevention and treatment of inflammation on a cellular and molecular level, by reducing lymphocyte infiltration and/or activation of macrophages and thereby reducing the release of inflammatory mediators. In other words, the fluorocarbon is used in the present invention as a primary anti-inflammatory agent.

Fluorocarbon molecules used in the present invention may have various structures, including straight or branched chain or cyclic structures as described by Riess, supra. These molecules may also have some degree of unsaturation, and may also contain bromine or hydrogen atoms, or they may be amine derivatives. Typically, the fluorocarbon is a liquid or a gas at room temperature (25° C). Preferably, the fluorocarbon has from about 2, 3, 4, or 5 carbon atoms to about 10, 12, or 14 carbon atoms. There are a number of fluorocarbons that are contemplated for use in the present invention. These fluorocarbons include bis(F-alkyl) ethanes such as $C_4F_9CH=CHCF_9$ (sometimes designated "F-44E"), $i\text{-}C_3F_7CH=CHC_6F_{13}$ ("F-i36E"), and $C_6F_{13}CH=CHC_6F_{13}$ ("F-66E"); cyclic fluorocarbons, such as C10F18 ("F-decalin", "perfluorodecalin" or "FDC"), F-adamantane ("FA"), F-methyladamantane ("FMA"), F-1,3-dimethyladamantane ("FDMA"), F-di- or F-trimethylbicyclo[3,3,1]nonane ("nonane"); perfluorinated amines, such as F-tripropylamine ("FTPA") and F-tri-butylamine ("FTBA"), F-4-methyloctahydroquinolizine ("FMOQ"), F-n-methyldecahydroisoquinoline ("FMIQ"), F-n-methyldecahydroquinoline ("FHQ"), F-n-cyclohexylpurrolidine ("FCHP") and F-2-butyltetrahydrofuran ("FC-75" or "RM101"), perfluorobutane, perfluoropropane, perfluoropentane, perfluorohexane, perfluoroheptane, or perfluorooctane. Both linear and branched isomers are contemplated.

Other suitable fluorocarbons may be selected from brominated perfluorocarbons, such as 1-bromoheptadecafluorooctane ($C_8F_{17}Br$, "PFOB", perflubron) 1-bromopenta-decafluorohexane ($C_6F_{13}Br$, "PFHB"). Other brominated fluorocarbons are disclosed in U.S. Pat. No. 3,975,512 to Long. Also contemplated are fluorocarbons having nonfluorine substituents, such as perfluorooctyl chloride, perfluorooctyl hydride, and having different numbers of carbon atoms, e.g., 6–12 carbon atoms.

Additional fluorocarbons contemplated in accordance with this invention include perfluoroalkylated ethers or polyethers, such as $(CF_3)_2CFO(CF_2CF_2)_2OCF(CF_3)_2$, $(CF_3)_2CFO(CF_2CF_2)_3OCF(CF_3)$, $(CF_3)CFO(CF_2CF_2)F$, $(CF_3)_2CFO(CF_2CF_2)_2F$, $(CF_{13})_2O$. Further, fluorocarbon-hydrocarbon compounds, such as, for example, compounds having the general formula $C_nF_{2n+1}\text{-}C_nH_{2n'+1}$, $C_nF_{2n+1}OC_n$, $H_{2n'+1}$, or $C_nF_{2n+1}CH=CHC_n,H_{2n'+1}$, where n and n' are the same or different and are from about 1 to about 10 (so long as the compound is a liquid or a gas at room temperature). Such compounds, for example, include $C_8F_{17}C_2H_5$ and $C_6F_{13}CH=CHC_6H_{13}$. It will be appreciated that esters, thioethers, and other variously modified mixed fluorocarbon-hydrocarbon compounds are also encompassed within the broad definition of "fluorocarbon" materials suitable for use in the present invention. Mixtures of fluorocarbons are also contemplated. Additional "fluorocarbons" not listed herein, but having those properties described in this disclosure that would lend themselves to use in accordance with the present invention are also contemplated. The fluorocarbon, in one preferred embodiment, is a perfluorocarbon or substituted perfluorocarbon.

The fluorocarbons used in the present invention may be used as neat liquid compositions, as gases, or as emulsions. Such emulsions are typically FC-in-water emulsions having a discontinuous fluorocarbon phase and a continuous aqueous phase. However, emulsions with a continuous fluorocarbon phase and a discontinuous aqueous phase are also contemplated. (Such reverse emulsions can be made in the form of gels, which are particularly suitable for topical applications.) The emulsions typically include emulsifying agents and osmotic agents, together with buffers and electrolytes. The FC emulsions may be selected from a wide range of suitable emulsions.

Although concentrations as low as 5% w/v are contemplated, in a preferred embodiment the concentrations are at least 25% or 30%, preferably at least 40%, 50%, 55%, and may be 60%, 75% or 80% w/v Emulsions of up to 85%, 90%, 100%, and 125% are also contemplated. Preferred fluorocarbon emulsion formulations include those disclosed in U.S. Pat. Nos. 4,865,836; 4,987,154; and 4,927,623, which are hereby incorporated by reference.

In treatment of mucosal inflammations, topical delivery of the FC is particularly preferred. The FC is simply brought into contact with the mucosal epithelium and allowed to remain in contact preferably for at least one minute, more preferably for an extended length of time (e.g., 30 minutes, one hour, or several hours). Suitable dosages depend on the surface area being treated, but are typically in the range of from about 0.01 g/kg to the entire lung volume of the patient (functional residual capacity or functional residual capacity plus tidal breathing volume). Treatment is continued as long as the inflammation persists.

In one embodiment of the invention, the fluorocarbon is administered as a liquid into the lungs of the patient, and then the patient breathes an oxygenated breathing gas while said fluorocarbon is still in the lungs.

The mode of FC delivery may, for example, be intratracheal in the case of pulmonary inflammatory conditions, orally or rectally in the case of gastrointestinal inflammation, topical in the case of epidermal inflammation, or intravenous, intramuscular intraarterial or subcutaneous in the treatment of either local or systemic inflammatory and autoimmune disorders.

In addition, the inhalation of FC-saturated vapor or FC droplets in the form of a mist or air-borne suspension delivered using a nebulizer or atomizer is particularly suitable for pulmonary inflammatory disorders. This mode of administration is particularly useful for treatment of acute pulmonary inflammation, such as during an asthma attack, when intratracheal intubation is not feasible. This mode of delivery has the advantage of not requiring a substantial liquid residual volume within the lung. The dosage for an adult human using this route can, for example, be from about 0.1 or 0.5 grams to about 10 grams or more per treatment.

In the treatment of gastrointestinal inflammation, the patient preferably swallows a neat fluorocarbon liquid. Alternatively, the fluorocarbon is a fluorocarbon emulsion. The quantity of fluorocarbon administered orally to an adult human would typically be from about 1 g to about 1000 g. In the treatment of acute peritonitis, the fluorocarbon liquid or emulsion is directly injected into the peritoneal cavity. The quantity injected can be from about 0.01 g/kg to about 10 g/kg, preferably about 1 g/kg to about 5 g/kg.

The most suitable route for administering systemic fluorocarbon is intravenous administration of fluorocarbon emulsion. Systemic dosages can be from about 0.01 g/kg to about 10 g/kg, preferably 0.1 g/kg to about 3.0 g/kg, based on the weight of the patient.

Inhalation of gas saturated with PFC vapor may also be used as a means for systemic treatment of inflammation. Breathing such a mixture will rapidly bring pulmonary tissue PFC gas tension to an equilibrium value set by alveolar gas tension. Saturation of body tissues and blood with PFC vapor to a partial pressure of about 5 or about 10 torr will modulate pulmonary and, it is believed, systemic immune function.

The invention also includes an apparatus or kit for delivering fluorocarbon into the lungs of a patient, comprising a container having fluorocarbon liquid inside, and means for atomizing, aerosolizing, or vaporizing the fluorocarbon liquid to deliver a unit dosage to the lungs of a patient. This apparatus may, for example, comprise a conventional atomizer or spray can filled with fluorocarbon liquid. Other types of devices for forming aerosols, mists, vapors, and the like are also well known and are contemplated for use in the present invention. The apparatus may also include means associated with the container for directing the fluorocarbon into the respiratory tract of the patient. Any conventional directing means may be used. For example, a mouthpiece, nozzle, or tube may be provided for this purpose. Alternatively, means for injecting or directing the mist or vapor into the breathing circuit of a conventional gas ventilator can also be provided. The unit dosage delivered by the apparatus is preferably from about 0.1 g to about 5 g. The container will typically contain from about 1 g to about 250 g of fluorocarbon, more preferably from about 2 g to about 100 g of fluorocarbon.

Although the inventors do not wish to be bound by any particular theory of the invention, it is believed that cell membrane phenomena may be involved in the anti-inflammatory action of fluorocarbons on cells. In particular, it is known that membranes of immune system cells include elements responsive to inflammatory stimulus and elements that release cytokines, adhesion molecules, and the like. The fluorocarbons of the present invention may become incorporated into the membranes of these cells, thereby interfering with the response of the cells to particular stimuli. This may be thought of as "stabilizing" the cell to prevent change in response to the stimulus in question.

EXAMPLE 1

Inhibition of HUVEC activation by PFOB

A single 100% w/v PFOB emulsion (Alliance Pharmaceutical Corp.) and a single vehicle (emulsifying agents with no PFOB) were tested in these studies. Several known human umbilical vein endothelial cells (HUVEC) were tested including bacterial endotoxin (LPS), interleukin-1 (IL-1), tumor necrosis factor (TNF) and phorbol myristate acetate (PMA). PFOB emulsion at various dilutions (1.25% v/v to 20% v/v) was added to HUVEC cultures prior to addition of an activating agent: LPS (100 ng/ml), IL-1 (5 units/ml), TNF (100 units/ml) or PMA (100 ng/ml). ICAM-1 and ELAM cell adhesion molecule expression was quantitated using ELISA.

Neither the PFOB emulsion nor the vehicle resulted in HUVEC activation as determined by the absence of ICAM-1 expression. PFOB did inhibit LPS-induced activation of HUVEC, as determined from ICAM-1 expression, in a dose-dependent manner (FIG. 1). At 10% v/v PFOB emulsion inhibited LPS activation by 95%, while at this same concentration vehicle inhibited LPS activation by only 7%.

Since the activation of endothelial cells by agents including LPS results in the expression of cell adhesion molecules including ICAM-1 and ELAM, and since cells expressing adhesion molecules are involved in the inflammatory response by attracting and adhering to leukocytes, the inhibition of this expression represents an anti-inflammatory effect. Thus, the addition of PFOB emulsion prior to LPS addition had a significant anti-inflammatory effect.

It was then determined whether this anti-inflammatory effect was due to a depression of macrophage phagocytic activity as described in the following example.

EXAMPLE 2

Depression of macrophage phagocytic activity by PFOB

Several groups of Male Wistar rats, each consisting of four animals, received either 3 g/kg body weight PFOB (Alliance Pharmaceutical Corp.) intravenously or were untreated. The colloidal carbon suspension was a commercial preparation of India ink which was centrifuged and diluted 1:10 in saline. Three to 24 hours and 2–8 days after PFC administration the carbon clearance from blood was determined from spectrophotometric measurements of diluted blood samples at 695 nm for the first 12 minutes after carbon injection. The clearance of administered carbon was expressed by the elimination constant k according to the equation $k=(\ln c_1 - \ln c_2)/(t_2-t_1)$, where $c_1$ and $c_2$ are concentrations at times $t_1$ and $t_2$.

Figure 2:
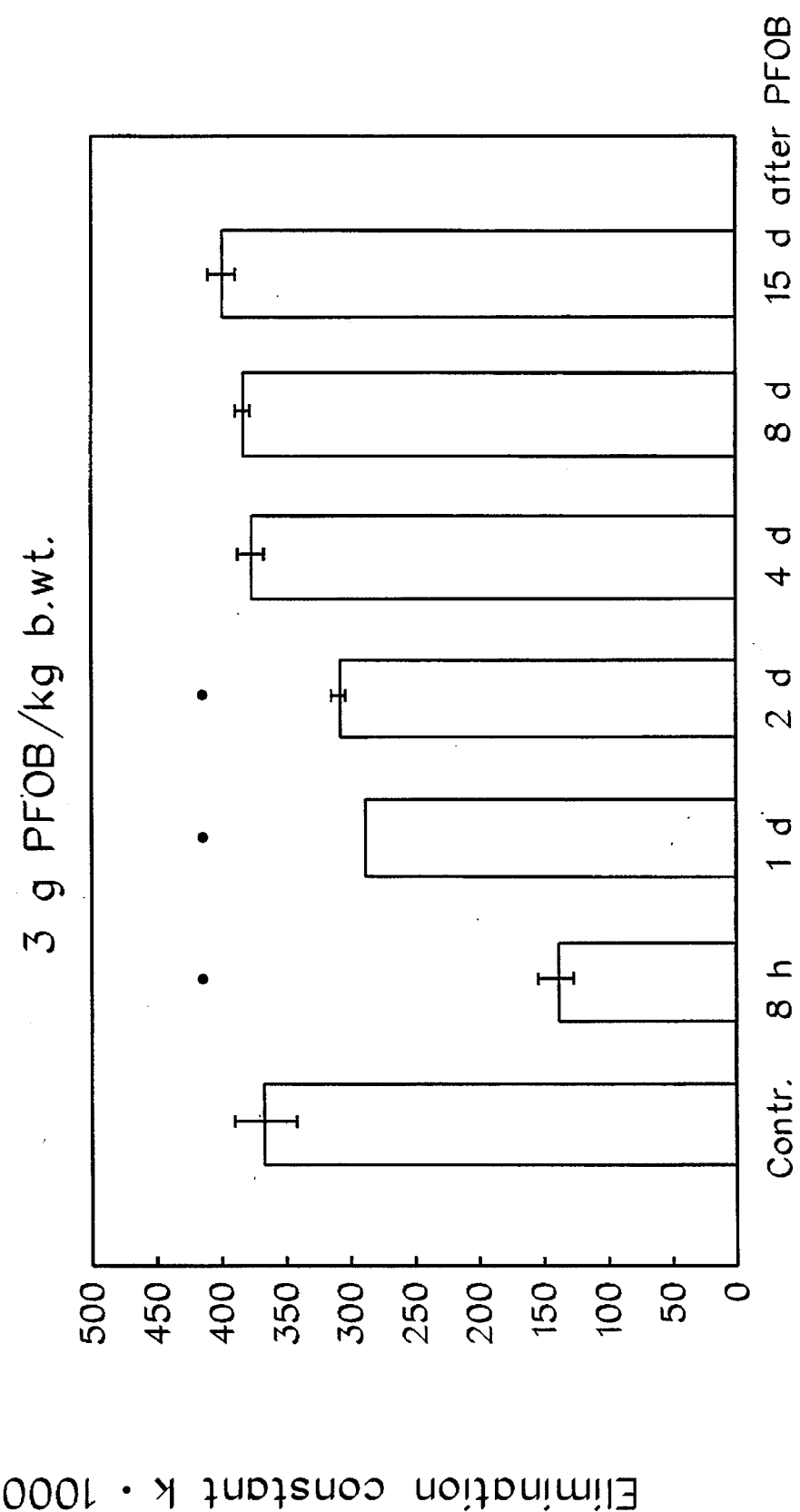
FIG. 2 shows the phagocytosis of colloidal carbon after administration of PFOB. The x-axis indicates the number of days after PFOB administration and the y-axis indicates the elimination constant.

A depression of the colloidal carbon clearance is an indirect indicator of depressed macrophage activity. A depression was noted for the first 3–24 hours. On the second day clearance returned to 85% of control (FIG. 2). After 4 days the PFOB-treated animals were at control levels.

Male Wistar rats were injected with 5 mg/kg body weight of $\gamma$-$Fe_2O_3$ particles and anesthetized with 30 mg/kg body weight of pentobarbital and magnetized in a 0.26 Tesla (2600 Gauss) field for 30 seconds. The animals were then placed in a magnetically shielded chamber and a depilated skin area above the right lower lip corner was brought in close contact to a double FOERSTER probe in a gradiometer mode of field detection. Different parameters were calculated using the curves of declining magnetism according to the equation $y = y_o e^{31\ kt} + C$ where y=total magnetic field strength at time t, $y_o$=dynamic field strength, k=relaxation constant, C=static field strength. The ratio $y_o/(y_o+C)$, the relation of dynamic to static magnetic field strength is a direct measure of liver macrophage activity.

PFOB (Alliance Pharmaceutical Corp.) was administered intravenously in a dose of 1 g/kg body weight. A control group did not receive PFOB. Longitudinal studies of the magnetic relaxation were performed in controls and test groups up to the 32nd day after injection.

Figure 3:
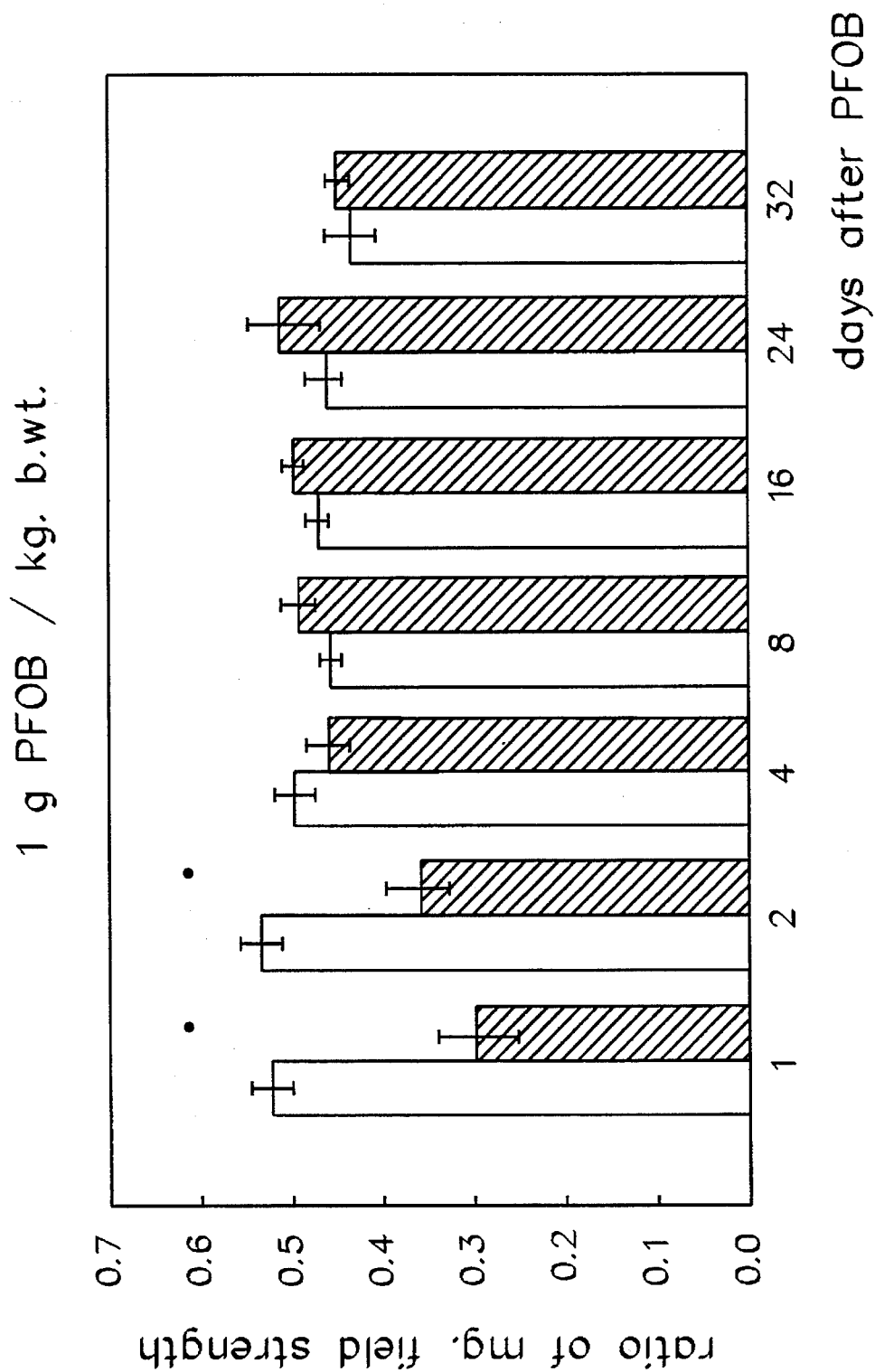
FIG. 3 shows the magnetometric measurement of macrophage activity in the liver after administration of PFOB. The x-axis indicates the number of days after PFOB administration and the y-axis indicates the ratio of magnetic field strength.

After administration of PFOB, the magnetic relaxation was decreased until the second day after injection (FIG. 3). This indicated that transient depression of liver macrophage activity occurred subsequent to PFOB administration. The transient nature of this effect is desirable so as not to dampen the host immune system for long periods of time.

To determine whether PFOB could reduce the inflammation associated with an acute inflammatory disorder, ARDS was induced in vivo and the effect of PFOB was determined as described in the following example.

EXAMPLE 3

Depression of pulmonary immune response by PFOB

Under $\alpha$-chloralose anesthesia (50 mg/kg) and metocurine iodide neuromuscular blockade (0.3 mg/kg), 14 piglets underwent tracheostomy; central venous, systemic and pulmonary arterial catheterization; and volume regulated continuous positive-pressure breathing using a conventional gas ventilator (Servo 900C, Siemens Elema) set at 25 breaths/minute, 4 cm $H_2O$ positive end-expiratory pressure, 10–15 ml/kg tidal volume and an inspiratory cycle of 25%. Homogenized gastric aspirate titrated to pH=1.0 was instilled into the tracheostomy tube of each subject at time zero (1 ml/kg) to induce ARDS. Hemodynamics, lung mechanics and gas exchange were evaluated every 30 minutes for 6 hours. Seven piglets were treated at 60 minutes by tracheal instillation of PFOB, a volume selected to approximate normal functional residual capacity of the lung, and were supported by perfluorocarbon assisted gas exchange (PAGE) without modifying ventilator settings. PFOB (2.5 ml/kg) was added to the trachea every hour to replace evaporative losses.

At the end of six hours, animals were sacrificed by bolus injection of potassium chloride. Lungs were examined and representative sections were placed in formaldehyde for later histological examination. Light microscopy sections were prepared for each animal, stained with hematoxylin and eosin, evaluated and photomicrographs taken.

On post-mortem visual examination of the lungs, atelectasis was observed in both groups to a greater degree in the untreated lung. The untreated lung was dark pink and had numerous fine spotty hemorrhagic areas throughout while the PAGE treated group had few hemorrhagic areas and a delicate pink translucent appearance. Microscopically, the untreated lung had areas of intense acute injury with many neutrophils and erythrocytes within and around poorly expanded alveoli, with areas of ruptured and thickened alveolar walls. Alveoli containing diffuse proteinaceous exudate were also observed. Conversely, in the PAGE-treated lung, the alveoli appeared thin-walled, more intact, and homogeneously well expanded without luminal neutrophils, erythrocytes and proteinaceous exudate. Thus, the absence of neutrophilic infiltration and subsequently resulting proteinaceous exudate provide direct evidence of the anti-inflammatory effect of PFOB.

Because these studies demonstrated a diminished neutrophil-induced pulmonary inflammatory response in animals given PFOB, and because alveolar macrophages produce free radicals which contribute to lung injury, it was also of interest to determine whether PFOB reduced inflammation by decreasing the production of inflammatory mediators in alveolar macrophages.

EXAMPLE 4

Depression of AM free radical production by PFOB

Alveolar macrophage (AM) function was assessed by determination of stimulated $H_2O_2$ and free radical (FR) production. AMs were isolated from adult rabbits via saline total lung lavage and were studied in five independent groups. For determination of $H_2O_2$ production, AMs (approximately $10^7$ cells) were rocked at 37° C. for 5 hours suspended in either minimal essential medium (MEM) or MEM plus PFOB (Alliance Pharmaceutical Corp.). Lipopolysaccharide (LPS, 50 µl) was added at 5 hours and the AMs were further incubated for 1 hour at which time assays were performed on cell-free supernatants. $H_2O_2$ production was determined by spectrophotometrically with a horseradish peroxidase/phenol red assay against known standards.

In a second set of studies, FR production was determined by chemiluminescence on $10^5$ cells using Luminol (300 µM) and zymosan. Approximately $2\times10^6$ AMs were incubated with MEM or MEM plus PFOB for up to four hours. The AMs were removed and FR production was measured after zymosan stimulation. Although aqueous cell suspensions and PFOB are immiscible, chemiluminescence was measured as above with increasing amounts of PFOB on a volume-to-volume basis added to the luminometer cuvette.

The untreated AMs produced 1.92 nanomoles $H_2O_2$ per $10^7$ cells versus 0.88 nanomoles for the PFOB treated cells. Incubation with PFOB resulted in a mean decrease of 91% in FR production compared to control animals at all time points. The depression of FR production by PFOB was dose-dependent. These findings suggested that the presence of PFOB in the lungs attenuated the ability of AMs to respond to stimuli and may play a role in reducing pulmonary inflammation during ventilation with PFOB.

The present invention has been described with reference to particular preferred embodiments; however, the scope of the invention is defined by the following claims and should be construed to include reasonable equivalents.

What is claimed is:

1. A method for reducing the inflammatory response in lung of a patient in need of such treatment, comprising the step of administering an effective, inflammation-reducing amount of a fluorocarbon gas or aerosol into said lung from an external source.

2. The method of claim 1, wherein said inflammation is associated with adult respiratory distress syndrome.

3. The method of claim 1, wherein said inflammation is associated with infant respiratory distress syndrome.

4. The method of claim 1, wherein said gaseous fluorocarbon is mixed with a breathing gas.

5. The method of claim 1, wherein said fluorocarbon is administered in the form of droplets suspended in a gas.

6. The method of claim 1, wherein the volume of said fluorocarbon is substantially less than the functional residual capacity of the lungs.

7. A method for reducing the inflammatory response in external epidermal or mucosal tissue, comprising the step of topically contacting said tissue with an effective inflammation-reducing amount of a liquid fluorocarbon.

8. A method for treating a systemic inflammatory disorder in a patient, comprising the step of administering to said patient an effective inflammation-reducing amount of a liquid fluorocarbon.

9. The method of claim 8, wherein said administering step is selected from the group consisting of intravenous, intramuscular, intraarterial and subcutaneous.

10. A method for reducing gastrointestinal inflammation in a patient, comprising orally or rectally administering to said patient an effective inflammation-reducing amount of a fluorocarbon liquid or emulsion.

* * * * *

UNITED STATES PATENT AND TRADEMARK OFFICE
CERTIFICATE OF CORRECTION

PATENT NO. : 5,470,885
DATED : November 28, 1995
INVENTOR(S) : Bradley P. Fuhrman, et. al.

It is certified that error appears in the above-indentified patent and that said Letters Patent is hereby corrected as shown below:

Title page, item [73], under assignee, after "Albany, N.Y.", insert-- and Alliance Pharmaceutical Corp., San Diego, Calif.--.

Signed and Sealed this

Fourth Day of June, 1996

Attest:

BRUCE LEHMAN

Attesting Officer    Commissioner of Patents and Trademarks